(12) United States Patent
Aygen

(10) Patent No.: US 7,762,957 B2
(45) Date of Patent: Jul. 27, 2010

(54) METHOD FOR MEASURING PANCREATIC METABOLISM

(75) Inventor: Sitke Aygen, Cologne (DE)

(73) Assignee: INFAI Institut fur biomedizinische Analytik und NMR-Imaging GmbH, Bochum (DE)

( * ) Notice: Subject to any disclaimer, the term of this patent is extended or adjusted under 35 U.S.C. 154(b) by 497 days.

(21) Appl. No.: 10/535,655

(22) PCT Filed: Nov. 10, 2003

(86) PCT No.: PCT/EP03/12515

§ 371 (c)(1),
(2), (4) Date: Aug. 16, 2005

(87) PCT Pub. No.: WO2004/043498

PCT Pub. Date: May 27, 2004

(65) Prior Publication Data

US 2006/0149159 A1   Jul. 6, 2006

(30) Foreign Application Priority Data

Nov. 12, 2002   (DE) ................. 102 52 390

(51) Int. Cl.
    *A61B 5/08*   (2006.01)
(52) U.S. Cl. .................. 600/532; 600/529; 422/84
(58) Field of Classification Search .............. 600/531; 422/84; 73/23.3; 436/900
    See application file for complete search history.

(56) References Cited

U.S. PATENT DOCUMENTS

2001/0021815 A1* 9/2001 Katzman et al. ............ 600/532

2003/0228647 A1* 12/2003 Asuka et al. ................. 435/23

FOREIGN PATENT DOCUMENTS

DE    44 26 204 A1    7/1993

OTHER PUBLICATIONS

Lembcke et al. "Exocrine pancreatic insufficiency: accuracy and clinical value of the uniformly labelled 13C-Hiolein breath test". 1996, Gut 39: 6680674. Downloaded from gut.bmj.com on Dec. 9, 2007.*

Mee et al. "Comparative study of pancreatic polypeptide (PP) secretion, endocrine and exocrine function, and structural damage in chronic alcohol induced pancreatitis (CAIP)". Gut 1983; 24; 642-647. downloaded from gut.bmg.com on Sep. 4, 2008.*

"Diagnostic Value of MTG-BT for the Dignosis of Exocrine Pancreatic Insufficiency in Comparison to Secretin Pancreozymin Test", S. Aygen et al.; Klinicka Biochemie A Metabolismus; vol. 5, p. 19-20; 1997; XP008027719.

"Comparative clinical evaluation of the 13C-mixed triglyceride breath test as an indiredct pacreatic function test"; Loser et al.; Scandinavian Journal of Gastroenterology; vol. 33, No. 3; p. 327-334; Mar. 1998; XP008027732.

"A mixed-triglyceride breath test for intraluminal fat digestive activity", Ghoos, et al.; Digestion vol. 22, No. 5; p. 239-247; 1981; XP008027842.

* cited by examiner

*Primary Examiner*—Patricia C Mallari
(74) *Attorney, Agent, or Firm*—Jacobson Holman PLLC

(57) ABSTRACT

Disclosed is a method for measuring pancreatic metabolism, which is characterized by the fact that the increase in $^{13}CO_2$ in the exhaled breath is determined prior to and following the intravenous application of secretin as well as prior to and following the oral application of a $^{13}C$ triglyceride.

10 Claims, 2 Drawing Sheets

METHOD FOR MEASURING PANCREATIC METABOLISM

This is a national phase of PCT/EP03/12515 filed Nov. 10, 2003.

The present invention relates to a method for measuring the metabolism of the pancreas in exocrine pancreatic insufficiency (EPI) of slight, moderate and severe degrees.

Exocrine pancreatic insufficiency is characterized by a reduction of enzyme release from the pancreas, especially amylase, lipase and chymotrypsin release, and the reduction of bicarbonate release.

The existing so-called "gold standard" of the determination of EPI comprises intravenously infusing secretin over a period of two hours and in the second hour additionally caerulein while the duodenal secretion is aspirated and analyzed through a duodenal probe. This determination method is tedious, expensive and very unpleasant to the patient and moreover interference prone. In addition, many patients exhibit an allergic reaction to caerulein. In addition, the test is interference prone and therefore subject to a considerable error rate. When there is no standardized performing of the test, its evaluation depends on the reference values established in the respective laboratory (see J.-Matthias Löhr: Exokrine Pankreasinsuffizienz, 1st Edition, Bremen: Uni-Med, 2001).

A simple test, but which is not very exact either, consists in the determination of elastase in the stool.

A pancreatic functional test in which amylase is determined mainly has been described in DE-C-44 26 204. In this test, natural corn starch is administered and, after metabolization, secreted through the exhaled air as $^{13}$C-enriched carbon dioxide, and analyzed. The test is based on the fact that corn starch is naturally enriched with $^{13}$C atoms.

A disadvantage of this test is that only severe degree exocrine pancreatic insufficiency can be determined thereby. Inter alia, this is due to the fact that the pancreas is not the only source of amylase and therefore the test is interfered with by amylase in the saliva and gastric secretion, cf. Löser et al., Z. Gastroenterol. 1997; 35: 187-194).

Further examinations of the functionality of the pancreas were developed with $^{14}$C- and $^{13}$C-enriched substances, the $^{13}$C-substances being preferred because they do not load the patient with the radioactive $^{14}$C isotope. As $^{13}$C-enriched test substances, cholesterol esters and triglycerides were mainly studied, and in particular, the mixed triglyceride glyceryl-1,3-dioctadecanoate-2-octanoate-1-$^{13}$C (also referred to as 1,3-distearyl-2-(carboxyl-$^{13}$C)octanoylglycerol) was studied because pancreatic lipase first hydrolyzes the two stearyl groups, and only then the shorter $^{13}$C-octanoyl group is subjected to metabolism.

Comparisons of the studies with the "gold standard" and other methods had the result that this method too is only suitable for diagnosing severe and, to some extent, moderate degree pancreatic insufficiency. In slight degree exocrine pancreatic insufficiency, this method fails (cf. Löser et al., Scand 3. Gastroenterol. 1998; 33: 327-334).

Thus, there is still a need for a simpler, and more convenient for the patient, determination method for the functionality of the pancreas, especially in cases of slight and moderate degree exocrine pancreatic insufficiency, by measuring the metabolism of the pancreas. The rating is effected as follows:

Slight Pancreatic Insufficiency:
  Reduction of bicarbonate by <50%
or
  Reduction of one enzyme by <50%
or
  Reduction of two enzymes by <25%
or
  Reduction of one enzyme and bicarbonate by <25%

Moderate Pancreatic Insufficiency:
  Reduction of more than two enzymes and/or bicarbonate by 25 to 75%

Severe Pancreatic Insufficiency:
  Reduction of all enzymes and/or bicarbonate secretion by >75%
  (Lankisch et al., Dig. Dis. Sci. 1983, 28: 490-493)

All calculations are based on the lower limits (mean value minus two sigma) of a normal universe.

It has now been found that the measurement is enabled by the fact that the increase of $^{13}CO_2$ in the exhaled air is determined before and after intravenous administration of secretin and before and after oral administration of a $^{13}$C-mixed triglyceride.

For determining the increase of $^{13}CO_2$ in the exhaled air, the ratio between $^{13}CO_2$ and $^{12}CO_2$ is preferably measured. Preferably, IRMS is employed for the measurement.

IRMS (isotope ratio mass spectrometry) has in the meantime become the most sensitive and best method for determining $^{13}CO_2$ in the exhaled air.

An alternative possibility is measurement by means of NDIR (non-dispersive infrared spectroscopy).

While according to a method of the prior art, such as that described in the above mentioned Löser et al. (1998) reference, only the $^{13}$C-enriched mixed triglyceride is administered and then the proportion of $^{13}CO_2$ in the respiratory air is measured, the method according to the invention is characterized in that the measurement is effected under the influence of previous secretin administration.

A reduced metabolization is indicated by a deficiency of pancreatic enzymes as seen by a delayed or reduced release of $^{13}CO_2$ as compared to healthy subjects, thus allowing a reliable diagnose.

In the method according to the invention, a breath sample is taken before the beginning of the test, and then further samples are taken at intervals of, for example, 15, 20 or 30 minutes. Usually, the measurement is effected for a period of from two to five hours, typically four hours.

Preferably, the administration of secretin is begun first, and then, the $^{13}$C-enriched mixed triglyceride is administered during the secretin administration or directly after the end thereof.

The exhaled air can be stored in sample containers and measured after the test has been completed. It is also possible to transport the respiratory air containers.

As the mixed triglyceride with $^{13}$C-labeling, those are preferably employed in which the acid in the 2-position bears the $^{13}$C-labels. Typically, in the triglyceride employed according to the invention, the 1 and 3 positions bear typical fatty acids with 12 to 20 carbon atoms which may also contain double bonds. In the 2 position of the triglyceride, there is a shorter acid with 2 to 12 carbon atoms. One particularly preferred mixed triglyceride is glyceryl-1,3-dioctadecanoate-2-octanoate-1-$^{13}$C, a mixed triglyceride which is available with high enrichment, for example, from Sigma-Aldrich.

In contrast to the "gold standard" in which secretin and then simultaneously caerulein must be infused in the course of two hours, the method according to the invention administers only secretin, and within a short time, preferably from 5 to 25 minutes, typically 15 minutes. The oral administration of the $^{13}$C-triglyceride is effected by means of a standardized test meal in the method according to the invention as well. Instead of the previously employed test meal consisting of 250 mg of mixed triglyceride homogenized with 10 g of chocolate cream in a 60° C. hot water bath and application after cooling to a piece of toast with 15 g of butter, this mixed triglyceride may preferably be administered more simply by stirring only 200 mg of mixed triglyceride, for example, with 15 g of corn starch, 3 g of cocoa powder and 15 g of butter in 20 ml of warm milk to obtain a homogeneous mixture, followed by spreading it on a slice of toast. The critical thing is not the amount of fat and oil, but the fact that the triglyceride can be easily mixed homogeneously with the other components and applied to a slice of toast. In principle, it is also possible to provide the mixed triglyceride in ready-packed portions with other stable and sufficiently fat-containing components, which only remains to be spread onto the slice of toast.

When the test results of the method according to the invention were compared with test results of the "gold standard", it has been found at first that although the correspondence is sufficient, it is still not fully satisfactory. Then, further studies have shown that the reproducibility of the method according to the invention is very high and the test results are thus much closer together than expected from the comparison with the "gold standard". When this astonishing result was checked, it was established that the "gold standard" evidently was never examined for its reproducibility because of its tediousness and unacceptability by the patient, and therefore, the deviations from the results of the method according to the invention are not to be attributed to the method according to the invention, but to error sources in the "gold standard" (cf. Exokrine Pankreasinsuffizienz 2001, Uni-Med Verlag AG, Bremen, Löhr J.-M. and Schneider H. T.).

Thus, the method according to the invention is superior to the "gold standard" in many respects: The placing of the duodenal probe, which is extraordinarily unpleasant for the patients, is dispensed with. The two-hour infusion of secretin and caerulein is dispensed with. Instead, only intravenous administration is effected within about 15 minutes, for example, and only of secretin. Since there are patients who can tolerate secretin, but not caerulein, there are substantially less studies which are discontinued for intolerance.

The cost for the test is about one tenth of the cost for the "gold standard". For the first time, it becomes possible to determine also slight degrees of exocrine pancreatic insufficiency, and to subject patients with this diagnosis to therapy. Moderate degree exocrine pancreatic insufficiency is also often curable or at least capable of stabilization. Severe degree pancreatic insufficiency generally can no longer be cured, but only treated for its symptoms. Of particular importance is the recognition in good time of the form of pancreatic insufficiency of slight and moderate degrees in children, all the more so since children can be cured better and more easily as compared to adults.

Thus, this simple method is also suitable as a follow-up of an enzyme substitution therapy.

According to the invention, a method for the determination of the functionality of the pancreas, namely the mild and moderate forms of exocrine pancreatic insufficiency, is provided.

EXAMPLE $^{13}$C Respiratory Test with Secretin Stimulation

Before the $^{13}$C-mixed triglyceride respiratory test is applied, the patient should be fasted for 6 hours (preferably over night). The test is to be performed in a resting position (sitting or lying).

The test begins with taking the first zero value respiratory sample ("zero value"). Thus, the patient blows into the sample container labeled "zero value" by means of a straw. Then, the patient is administered 1 U of secretin per kg of body weight intravenously over 15 min.

Secretin can be obtained, for example, as Secrelux® from Goldham Pharma GmbH, Germany. One CU (clinical unit) corresponds to 1 U (unit).

The patient now ingests the prepared test meal within 10 minutes.

During the next four hours after the end of the test meal, respiratory samples are taken at the times established in the protocol and in the way as described above into the sample containers, which are each unambiguously labeled.

Sample Taking:

| 00 min | 15 min secretin i.v. | 10 min test meal | 15 min | 30 min | 50 min | 70 min | 90 min | 110 min | 130 min | 150 min | 170 min | 190 min | 210 min | 230 min |
|---|---|---|---|---|---|---|---|---|---|---|---|---|---|---|

Figure 1:
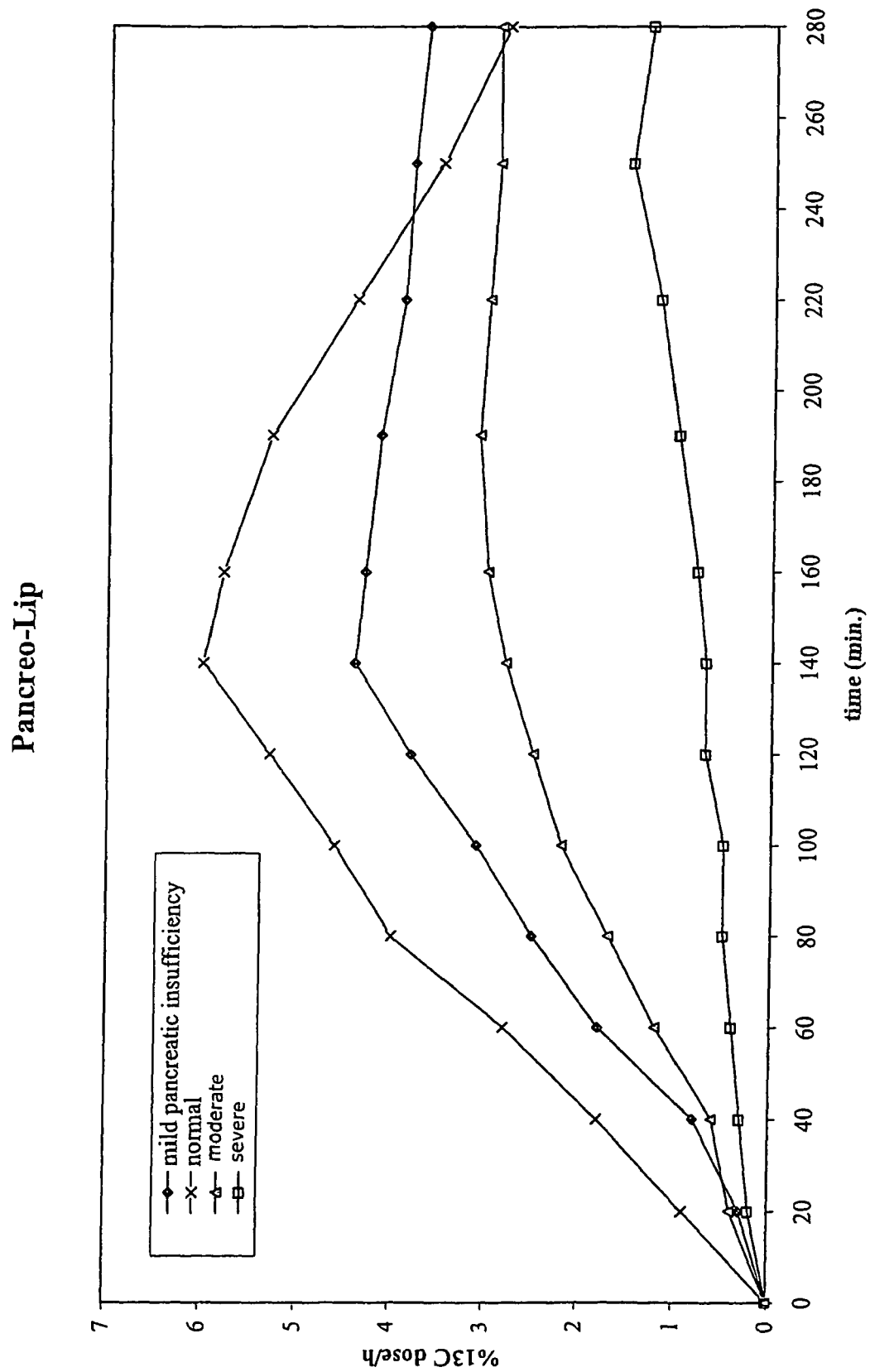
FIG. 1 shows the results of the $^{13}CO_2$ respiratory air values for a healthy subject (x) and for a subject with slight (♦), moderate (▲) and severe (□) degree EPI.
Figure 2:
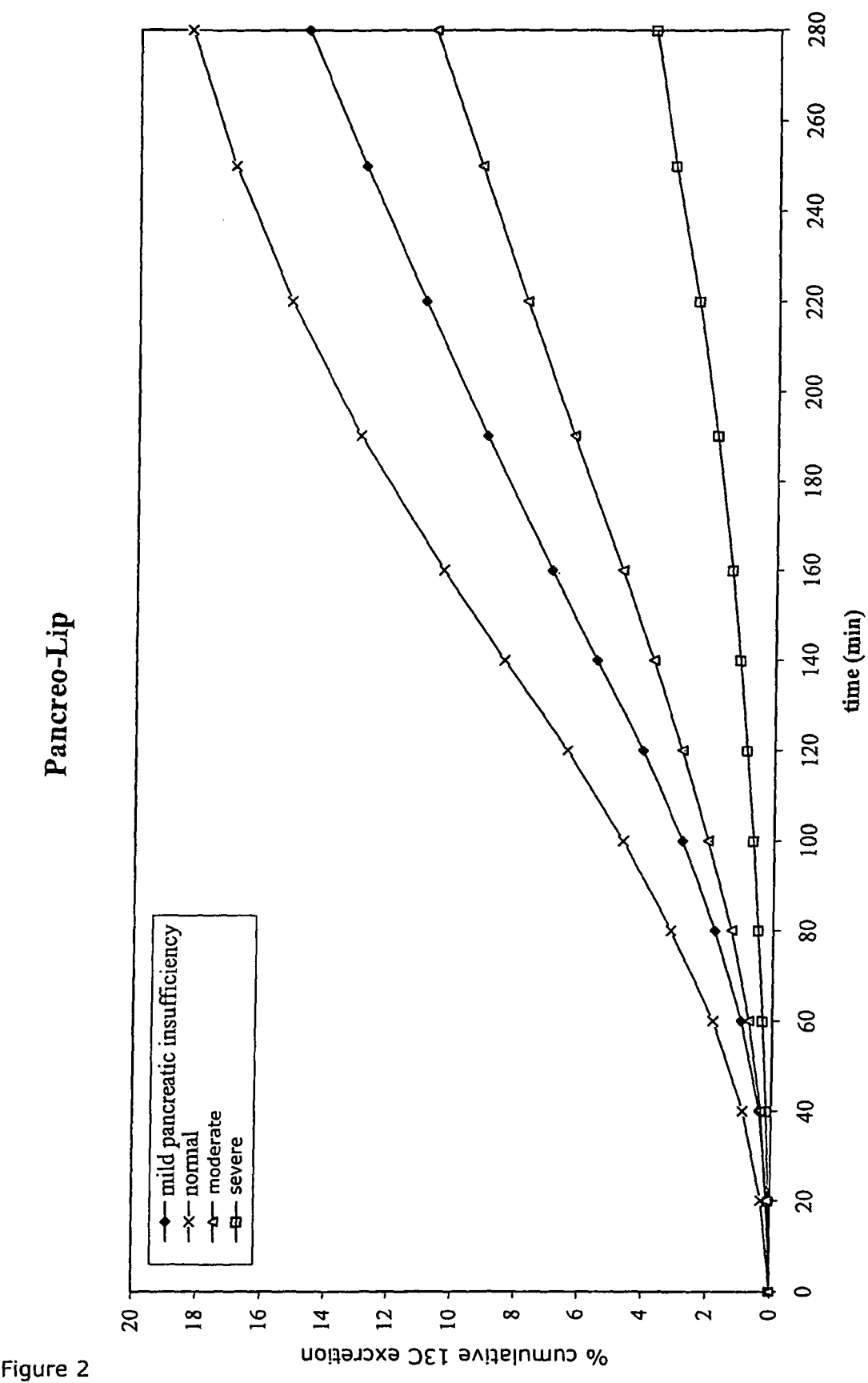
FIG. 2 shows the cumulative $^{13}CO_2$ respiratory air values for a healthy subject (x) for a subject with slight (♦), moderate (▲) and severe (□) degree EPI.

The invention claimed is:

1. A method for measuring an induced release of $^{13}CO_2$ comprising:
   measuring the release of $^{13}CO_2$ in exhaled air of a subject, followed by
   inducing the release of $^{13}CO_2$ in exhaled air of a the subject by intravenous administration of secretin and oral administration of a $^{13}$C-triglyceride to the subject, and
   measuring the release of $^{13}CO_2$ in the exhaled air of the subject after the intravenous administration of secretin and the oral administration of the $^{13}$C-triglyceride to the subject.

2. The method according to claim 1 characterized in that the $^{13}$C-triglyceride is the mixed triglyceride glyceryl-1,3-dioctadecanoate-2-octanoate-1-$^{13}$C.

3. The method according to claim 1 characterized in that measuring the amount of $^{13}CO_2$ is effected by isotope ratio mass spectrometry (IRMS) or non-dispersive infrared spectroscopy (NDIR).

4. The method according to claim 1 wherein the intravenous administration comprises intravenously administering to the subject 1 clinical unit (U) of secretin per kilogram of body weight of the subject within about 15 to 30 minutes.

5. The method according to claim 2 wherein the oral administration comprises orally administering to the subject 200 mg of the mixed triglyceride with a test meal.

6. A method for diagnosing exocrine pancreatic insufficiency (EPI), comprising:

measuring $^{13}CO_2$ in exhaled air of a subject, followed by inducing the release of $^{13}CO_2$ in exhaled air of the subject by intravenous administration of secretin and oral administration of a $^{13}C$-triglyceride to the subject, measuring the induced value of $^{13}CO_2$ in the exhaled air of the subject after intravenous administration of secretin and oral administration of the $^{13}C$-triglyceride to the subject, and comparing (i) the measured induced value of $^{13}CO_2$ in exhaled air of the subject with (ii) a measured induced value of $^{13}CO_2$ in exhaled air of a healthy subject after intravenous administration of secretin and after oral administration of the $^{13}C$-triglyceride to the healthy subject, wherein a diagnosis of EPI in the subject is indicated when the induced value of $^{13}CO_2$ in the subject is reduced as compared to the healthy subject.

7. The method according to claim 6 characterized in that the $^{13}C$-triglyceride is the mixed triglyceride glyceryl-1,3-dioctadecanoate-2-octanoate-1-$^{13}C$.

8. The method according to claim 6 characterized in that measuring the amount of $^{13}CO_2$ is effected by isotope ratio mass spectroscopy (IRMS) or non-dispersive infrared spectroscopy (NDIR).

9. The method according to claim 6 wherein the intravenous administration comprises intravenously administering to the subject 1 clinical unit (U) of secretin per kilogram of body weight of the subject within about 15 to 30 minutes.

10. The method according to claim 9 wherein the oral administration comprises orally administering to the subject 200 mg of the mixed triglyceride with a test meal.

* * * * *